US00PP36616P3

(12) United States Plant Patent
Volz

(10) Patent No.: US PP36,616 P3
(45) Date of Patent: Apr. 22, 2025

(54) APPLE TREE NAMED 'PremA133'

(50) Latin Name: *Malus domestica*
Varietal Denomination: PremA133

(71) Applicant: Prevar Limited, Hastings (NZ)

(72) Inventor: Richard Volz, Havelock North (NZ)

(73) Assignee: Prevar Limited, Hastings (NZ)

( * ) Notice: Subject to any disclaimer, the term of this patent is extended or adjusted under 35 U.S.C. 154(b) by 0 days.

(21) Appl. No.: 18/798,378

(22) Filed: Aug. 8, 2024

(65) Prior Publication Data

US 2025/0081867 P1 Mar. 6, 2025

(30) Foreign Application Priority Data

Sep. 5, 2023 (FR) ..... PBR 21414

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 6/7418; A01H 5/08
See application file for complete search history.

*Primary Examiner* — Keith O. Robinson
(74) *Attorney, Agent, or Firm* — Michelle Bos Legal LLC

(57) ABSTRACT

A new and distinct apple tree named 'PremA133' notable for its fruit, which has an attractive red skin color, appealing flavor, and large size, and for its double resistance to apple scab (*Venturia inaequalis*).

7 Drawing Sheets

Latin name: *Malus domestica.*
Variety denomination: PremA133.

BACKGROUND AND SUMMARY OF THE VARIETY

The new apple tree 'PremA133' was created in the course of a planned breeding program carried out at Havelock North, New Zealand. 'PremA133' originated from a controlled cross of 'A180R20T066' (seed parent, not patented) and 'A185R09T179' (pollen parent, not patented) performed at Havelock North, New Zealand in October 2008. 'PremA133' was selected from a population of seedlings derived from the parents, and was singled out for further observation for its fruit, which has an attractive red skin color and appealing flavor. The variety was first asexually propagated by grafting onto 'M9' rootstock (not patented) at Havelock North, New Zealand in August 2015. 'PremA133' trees have been observed over a number of asexually propagated generations, and have been found to remain true to type.

The 'PremA133' apple tree is distinguished by its fruit, which exhibits a solid flush red skin color and an acidic-tangy flavor. It is further distinguished by having both the Vf and Vh2 scab resistance genes, which together imbue the 'PremA133' apple tree with "double" resistance to apple scab (*Venturia inaequalis*), resulting in decreased reliance on chemical applications to control scab. In comparison, female parent 'A180R20T066' bears mild-flavored, yellow-skinned fruit, and carries only the Vf scab resistance gene. Male parent 'A18R09T179' bears only the Vh2 scab resistance gene.

'PremA133' is distinguished from similar varieties as set forth in Table 1 below.

TABLE 1

Comparison of 'PremA133' to Similar Varieties

| Comparison Variety | Characteristic | In Comparison Variety | In 'PremA133' |
|---|---|---|---|
| 'PremA134' (not patented) | Lenticel Prominence | Low | High |
| 'PremA129' (USPP 29,214) | Red Skin Color | Red | Pink-Red |
| 'Sciros' (USPP 7,814) | Maturity Time | Early to mid-September | Early October |
| 'Cripps Pink' (USPP 7,880) | Maturity Time | Late October to early November | Early October |

BRIEF DESCRIPTION OF THE PHOTOGRAPHS

The attached photographs of trees and fruit were taken at Havelock, New Zealand during the 2023/2024 growing season. The trees depicted were planted in 2018 and grown on 'M9' rootstock (not patented).

DETAILED BOTANICAL DESCRIPTION OF THE VARIETY

Figure 1:
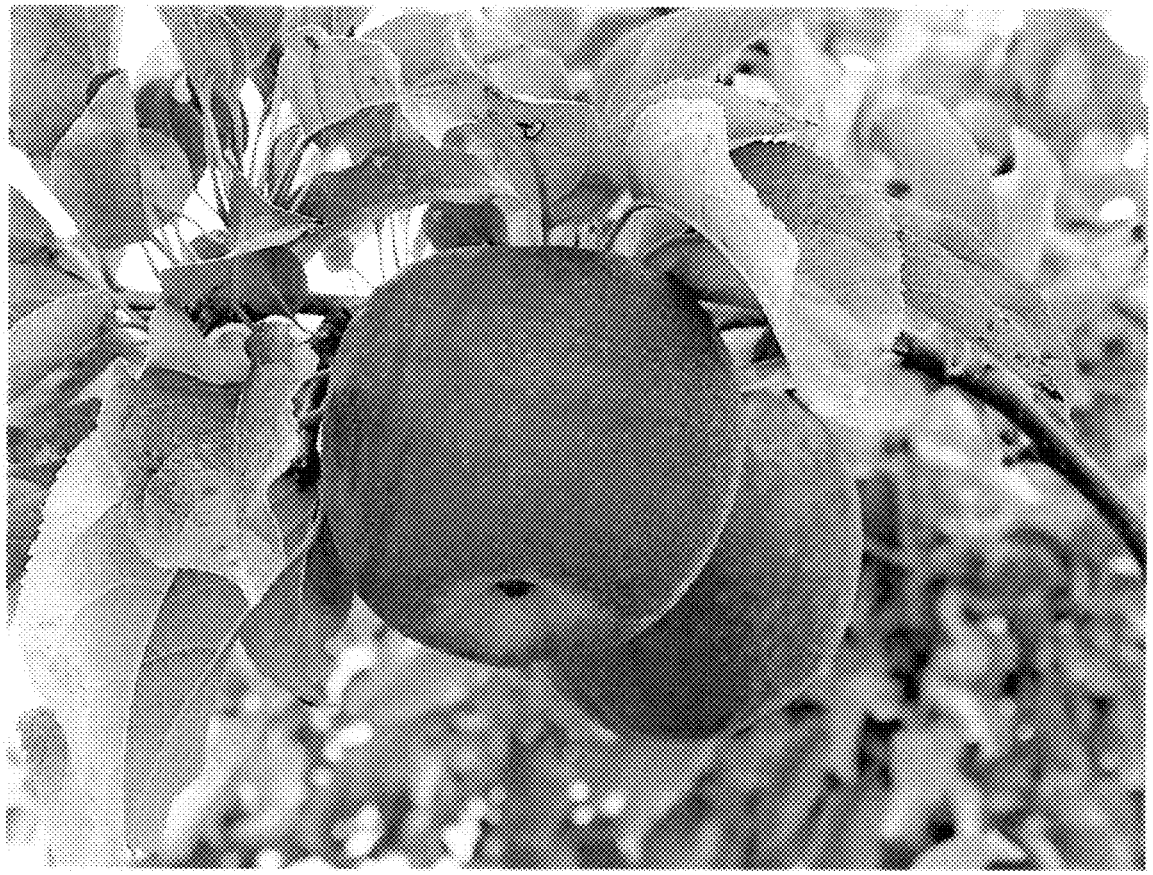
FIG. 1 shows the fruit of a 'PremA133' apple tree.
Figure 2:
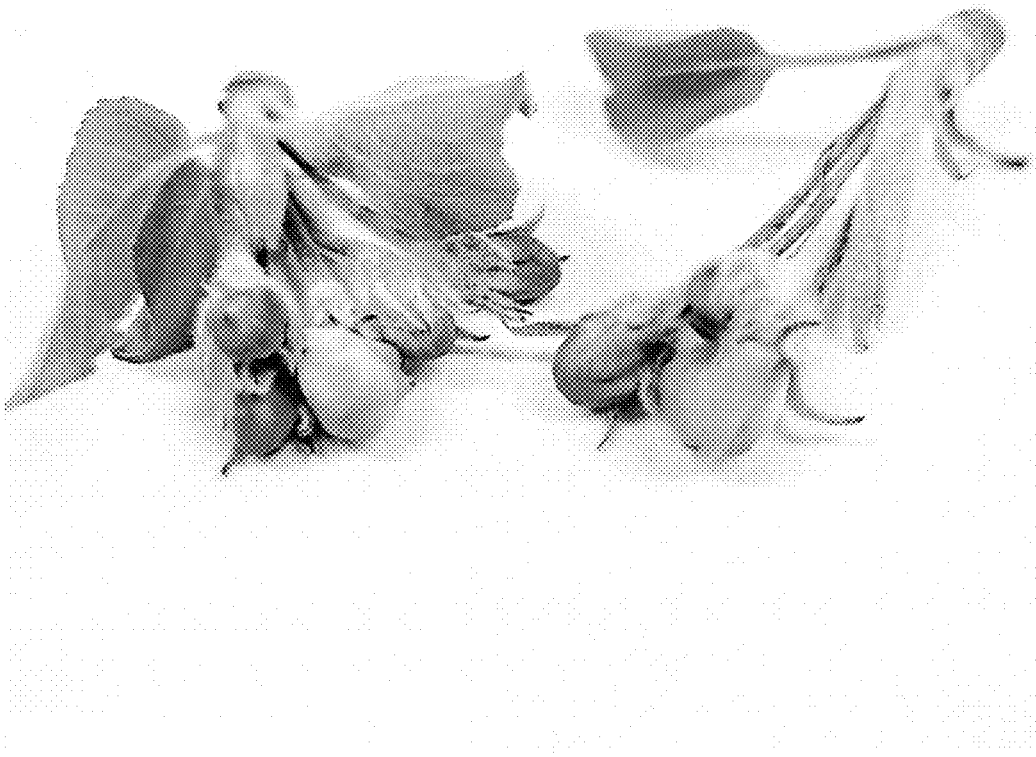
FIG. 2 shows the flower buds of a 'PremA133' apple tree.
Figure 3:
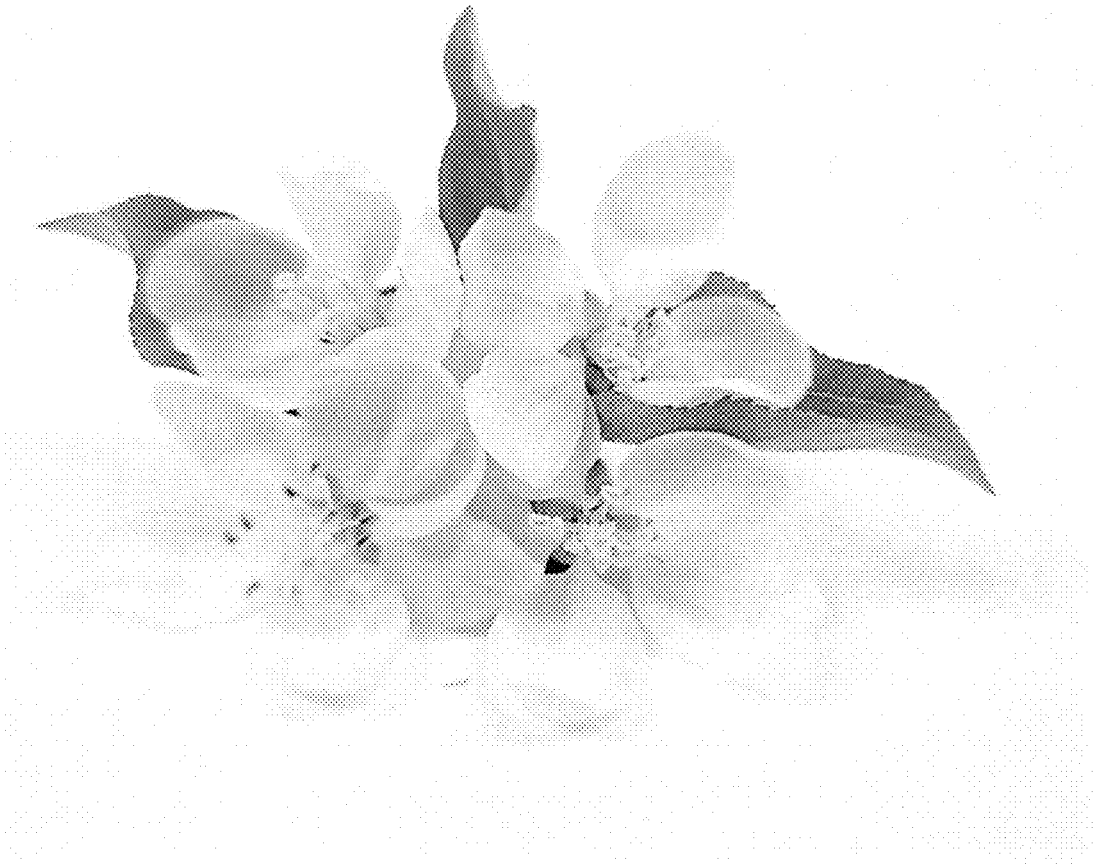
FIG. 3 shows the flowers of a 'PremA133' apple tree.
Figure 4:
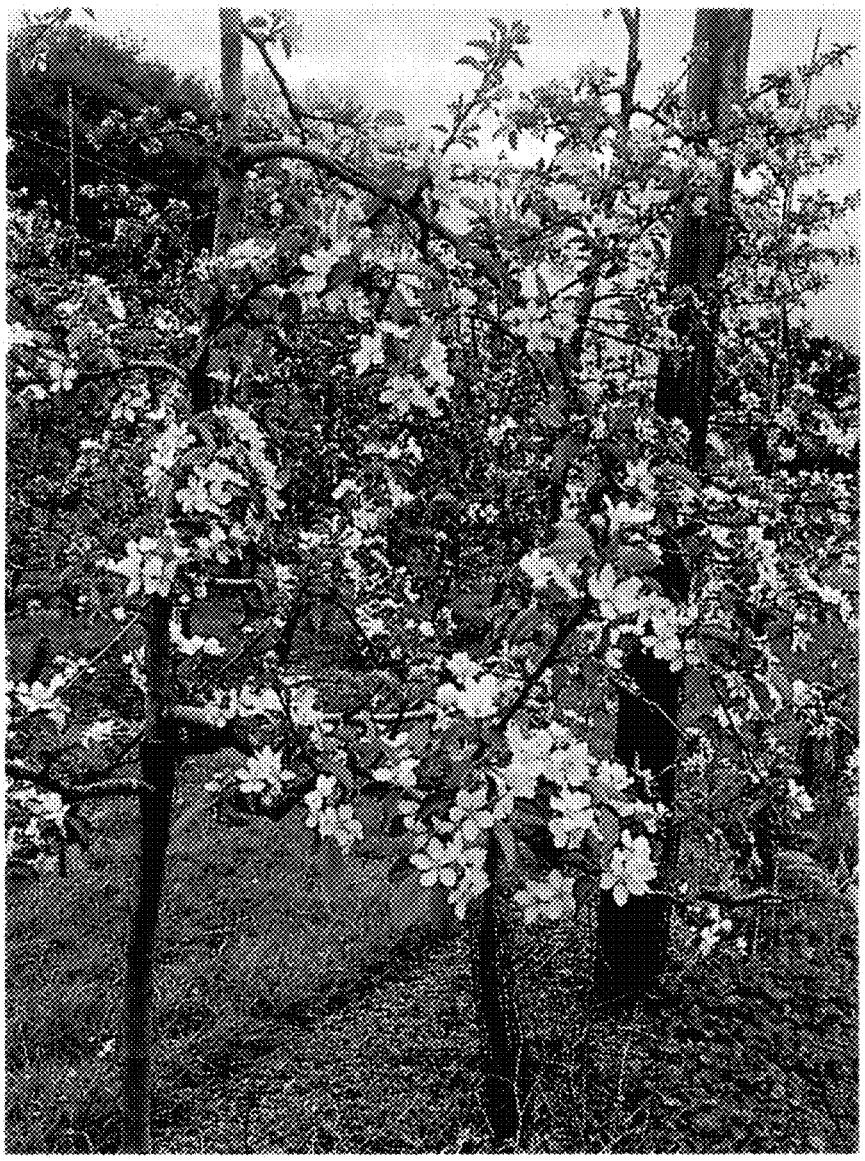
FIG. 4 shows five-year-old 'PremA133' apple trees in bloom.
Figure 5:
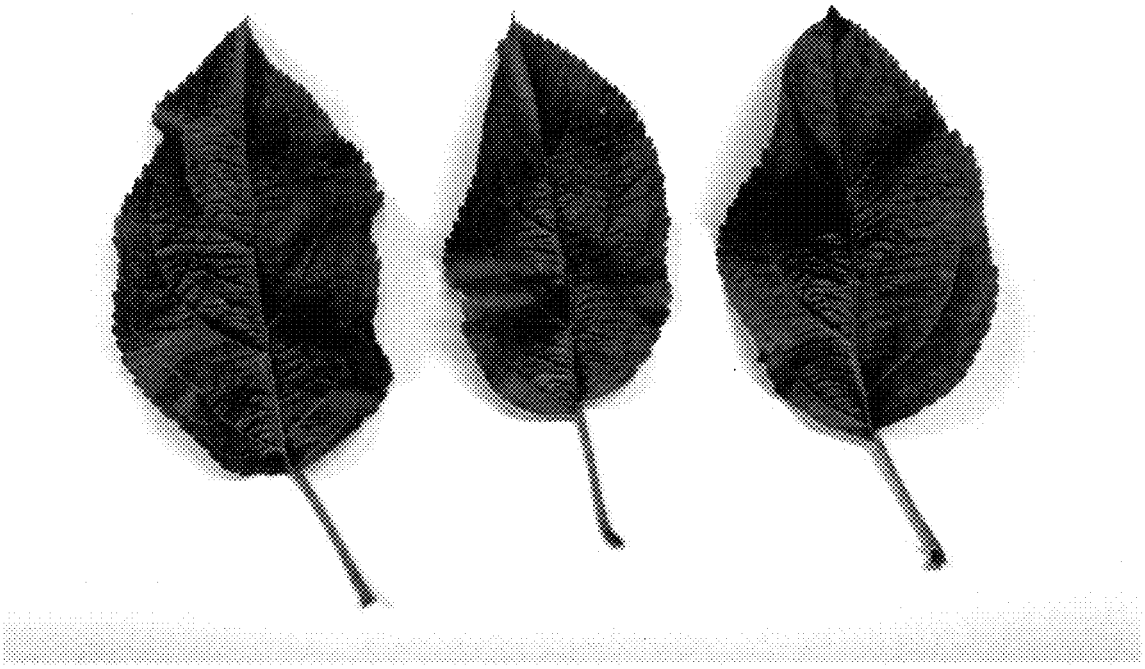
FIG. 5 shows the upper surface of leaves of a 'PremA133' apple tree.
Figure 6:
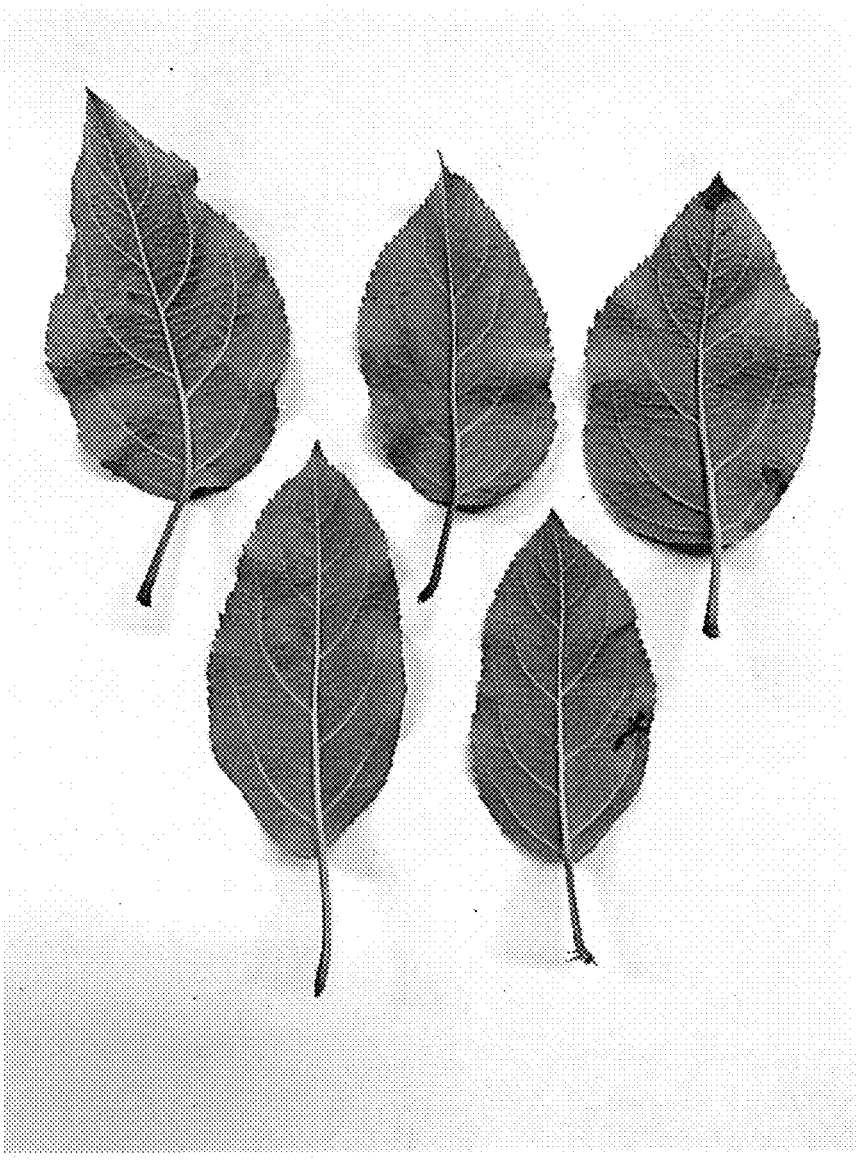
FIG. 6 shows the lower surface of leaves of a 'PremA133' apple tree.
Figure 7:
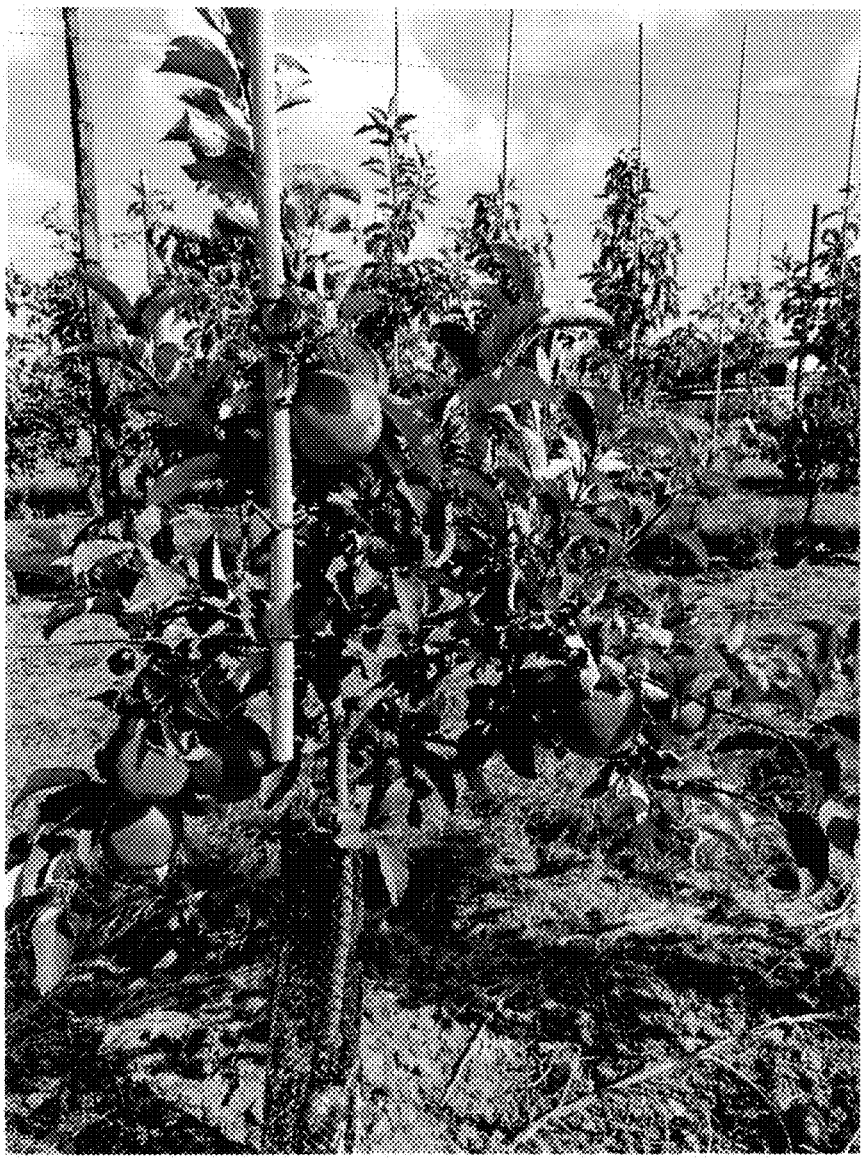
FIG. 7 shows a five-year-old 'PremA133' apple tree and its fruit.

The following detailed botanical description is based on five-year-old trees and fruit observed at Havelock, New Zealand during the 2023/2024 growing season. The described trees were planted in 2018 and grown on 'M9' rootstock (not patented). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average. All colors are described with reference to The R.H.S. Colour Chart, 6$^{th}$ ed. (Royal Horticultural Society, 2015).

Tree:
- *Vigor*.—Medium.
- *Type*.—Ramified.
- *Habit*.—Spreading.
- *Height*.—1.8 m.
- *Spread*.—3.2 m.
- *Trunk diameter* (*at* 30 *cm above the graft*).—12.7 cm.
- *Bearing*.—On spurs.
- *Bark texture*.—Smooth to medium with raised lenticels.
- *Bark color*.—Greyed-green 197B; with pubescence removed, grey-brown 199B.
- *Lenticel length*.—1.4 mm to 1.7 mm.
- *Lenticel width*.—0.4 mm to 0.6 mm.
- *Lenticel shape*.—Elongated.
- *Lenticel color*.—Greyed-white 156C.
- *Lenticel density*.—45 per 10 cm$^2$.

Branch (fruiting branches located at around 1 m above the graft union):
- *Length*.—89 cm.
- *Diameter*.—20 mm.
- *Crotch angle*.—75° to 85° (trained).
- *Bark color*.—Grey brown N199D (pubescence removed).
- *Branch lenticel length*.—0.9 mm to 1.2 mm.
- *Branch lenticel width*.—0.4 mm to 0.6 mm.
- *Branch lenticel shape*.—Elongated.
- *Branch lenticel color*.—Brown N200B.
- *Branch lenticel density*.—5 to 7 per cm$^2$.

One year old shoot:
- *Length*.—48 cm.
- *Diameter*.—9 mm.
- *Internode length*.—3 cm.
- *Color*.—Grey-brown N199C.
- *Pubescence*.—Sparse, moderate.
- *Shoot lenticel length*.—0.8 mm to 1.1 mm.
- *Shoot lenticel width*.—<0.5 mm.
- *Shoot lenticel shape*.—Round to elongated.
- *Shoot lenticel density*.—5 per cm$^2$.

Flower buds:
- *Stage described*.—First pink.
- *Quantity per spur*.—Average 5.
- *Bud shape*.—Obovate.
- *Apex shape*.—Rounded.
- *Length*.—8.4 mm.
- *Diameter*.—5.0 mm.
- *Color*.—Red 39B.

Flowers:
- *Diameter of fully open flower*.—41 mm.
- *Depth of fully open flower*.—10 mm.
- *Relative position of petal margins*.—Free.
- *Quantity per cluster*.—Average 5.
- *Date of first bloom*.—October 12 (2023).
- *Date of full bloom*.—October 12 (2023).
- *Pollination requirement*.—'Fuji' (not patented) and other late flowering varieties.

Petals:
- *Quantity per flower*.—5.
- *Petal shape*.—Obovate.
- *Length*.—17 mm.
- *Width*.—12 mm.
- *Apex shape*.—Obtuse.
- *Base shape*.—Acute.
- *Margin*.—Weak undulation; curled.
- *Color of upper surface*.—White NN155D.
- *Color of lower surface*.—White NN155B with minimal weak veins red-purple 76C.

Pitsils:
- *Length*.—9.7 mm.
- *Color*.—Yellow-green N144A.

Stigma:
- *Diameter*.—<0.5 mm.
- *Color*.—Yellow-green 151A.

Style:
- *Length*.—7.6 mm.
- *Color*.—Yellow-green N144A.

Stamens:
- *Quantity*.—Average 20.
- *Length*.—7.3 mm.
- *Anther color*.—Yellow-green 153D.
- *Pollen*.—Moderate.
- *Pollen color*.—Yellow 8B.

Pedicel:
- *Length*.—23.8 mm.
- *Diameter*.—1.4 mm.
- *Color*.—Greyed orange 174A with pubescence.

Sepals:
- *Quantity*.—5.
- *Color*.—Yellow-green 150A.
- *Shape*.—Acute triangular.
- *Apex shape*.—Acute.
- *Margin*.—Smooth, reflexed.

Leaves:
- *Shape*.—Ovate.
- *Length*.—10 cm.
- *Width*.—5.7 cm.
- *Blade margin*.—Serrate.
- *Apex*.—Acuminate.
- *Base shape*.—Rounded.
- *Color of upper surface*.—Green N137B.
- *Color of lower surface*.—Yellow-green 144A.
- *Pubescence*.—Moderately present on lower surface.
- *Attitude in relation to shoot*.—Upward.

Petiole:
- *Length*.—28.7 mm.
- *Diameter*.—1.8 mm.
- *Color*.—Yellow-green N144C with moderate to high anthocyanin coloration purple N79C.

Fruit:
- *Quantity per cluster*.—2 to 3 (after thinning).
- *Diameter*.—77 mm.
- *Height*.—66 mm.
- *Weight*.—204 g.
- *General shape in profile*.—Globose.
- *Position of maximum diameter*.—Near equator.
- *Ribbing*.—Weak.
- *Crowning at calyx end*.—Weak.
- *Size of eye*.—Small.

*Aperture of eye*.—Closed.
*Depth of eye basin*.—10 mm.
*Width of eye basin*.—32.4 mm.
*Length of sepal*.—4 mm to 5 mm.
*Bloom of skin*.—Present, moderate.
*Greasiness of skin*.—Absent or weak.
*Background color of skin*.—Yellow-green 154C.
*Amount of overcolor*.—Large to very large, 90%.
*Overcolor of skin*.—Red 53C.
*Intensity of over color*.—Moderate to Intense.
*Pattern of over color*.—Solid flush.
*Number of lenticels*.—Few to medium, about 5 per $cm^2$.
*Diameter of lenticels*.—Medium to large, about 0.4 mm.
*Amount of russet around stalk cavity*.—Absent.
*Amount of russet on cheeks*.—Absent or weak.
*Amount of russet around eye basin*.—Absent or weak.
*Length of stalk*.—24.3 mm.
*Thickness of stalk*.—2.3 mm.
*Depth of stalk cavity*.—17.6 mm.
*Width of stalk cavity*.—34.5 mm.
*Stalk color*.—Grey-brown N199D.
*Firmness of flesh*.—Firm, 8.15 $kgf/cm^2$.
*Flesh texture*.—Fine to medium.
*Juiciness*.—Moderate.
*Flavor*.—Acidic-tangy.
*Aroma*.—Mild citrus.
*Brix*.—13.8° Brix.
*Flesh color*.—Yellow-white 158C.

Seeds:
*Quantity per fruit*.—5 to 7.
*Shape*.—Ovate.
*Length*.—9 mm to 10 mm.
*Width*.—4 mm to 6 mm.
*Color*.—Greyed-orange 166C.

Harvest:
*Time for harvest*.—March 12 (2024, Havelock North, New Zealand); after 'PremA96' (U.S. Plant Pat. No. 24,946), before 'Scilate' (U.S. Plant Pat. No. 20,477).
*Number of picks*.—One.
*Yield per tree*.—80+ fruits.

Disease and pest resistance: Double apple scab (*Venturia inaequalis*) resistance (carries Vh2 and Vf genes).
Storage characteristics: 6 months in 1-MCP storage.
Market use: Fresh.

I claim:

1. A new and distinct apple tree named 'PremA133', substantially as described and illustrated herein.

* * * * *